United States Patent

Gianakos

[11] Patent Number: 5,195,993
[45] Date of Patent: Mar. 23, 1993

[54] NEEDLE PROTECTING ASSEMBLY

[76] Inventor: Arthur Gianakos, 6 White Fir Dr., Loudonville, N.Y. 12211

[21] Appl. No.: 575,226

[22] Filed: Aug. 30, 1990

[51] Int. Cl.$^5$ .......................................... A61M 25/00
[52] U.S. Cl. .................................. 604/283; 604/411; 604/905; 604/198; 128/919
[58] Field of Search .................. 604/192, 195–198, 604/240, 263, 905, 283, 280, 83, 86, 411–414; 128/919

[56] References Cited

U.S. PATENT DOCUMENTS

| 4,005,710 | 2/1977 | Zeddies et al. | 604/86 |
|---|---|---|---|
| 4,116,196 | 9/1978 | Kaplan et al. | 604/192 |
| 4,232,669 | 11/1980 | Nishke | 604/192 |
| 4,373,526 | 2/1983 | Kling | 604/198 X |
| 4,511,359 | 4/1985 | Vaillancourt | 604/411 |
| 4,631,057 | 12/1986 | Mitchell | 604/198 |
| 4,681,567 | 7/1987 | Masters et al. | 604/198 |
| 4,752,292 | 6/1988 | Lopez et al. | 604/244 |
| 4,932,944 | 6/1990 | Jagger et al. | 604/192 |
| 4,946,445 | 8/1990 | Lynn | 604/192 |
| 4,964,855 | 10/1990 | Todd et al. | 604/283 |
| 4,981,469 | 1/1991 | Whitchouse et al. | 604/86 |
| 4,998,913 | 3/1991 | Vaillancourt | 604/283 |
| 4,998,921 | 3/1991 | Vickroy et al. | 604/167 |
| 4,998,925 | 3/1991 | Al-Sionti et al. | 604/283 |
| 4,998,927 | 3/1991 | Vaillancourt | 604/283 |
| 5,011,475 | 4/1991 | Olsun | 604/192 |

FOREIGN PATENT DOCUMENTS 8910770 11/1989 World Int. Prop. O. ........... 604/192

Primary Examiner—John D. Yasko
Assistant Examiner—Mark O. Polutta
Attorney, Agent, or Firm—Roger S. Thompson

[57] ABSTRACT

A needle protective assembly includes a ratchet and pawl arrangement for permitting the unidirectional movement of a protective sleeve along a body of a dispenser, such as a hypodermic syringe. The sleeve is adapted to cover a standard Y-site diaphragm, and includes a lock to secure the sleeve to the Y-site while in use. The assembly may also include indicia on the exterior thereof to measure the amount of needle exposed beyond the end of the sleeve, if the sleeve is not in its fully extended position. The assembly may further include a luer lock, for attaching the assembly to pre-existing standardized fittings.

3 Claims, 2 Drawing Sheets

NEEDLE PROTECTING ASSEMBLY

BACKGROUND OF THE INVENTION

The present invention relates to medical devices and, more particularly, to devices for protecting against the accidental puncturing of one's skin by the tip of a needle, such as used in a hypodermic syringe.

Hypodermic syringes are commonly used in medicine for dispensing medicines or other fluids into patients, either intravenously or intramuscularly. There is one hazard to their use, however. The sharp needle may prick the skin of the physician or nurse. Now that so many dangerous and highly contagious diseases are prevalent, particularly acquired immune deficiency syndrome (AIDS), it has become increasingly worrisome to many practitioners to dispense fluids by use of hypodermic needles. Still, there is no effective substitute.

Thus, there is a need for a device which may render the use of needles, such as those used with hypodermic syringes and the like, less dangerous.

Many devices have been developed to shield the tip of a hypodermic needle after it has been exposed to potentially dangerous contaminants. These devices include many different types of sheaths and covers, and are generally retractable, to permit the use of the syringe. Such devices commonly include some slidable sheath capable of movement between an extended position in which the tip of the needle is covered, to a retracted position in which the tip is exposed, so that the needle may be used.

For example, U.S. Pat. No. 4,874,383 discloses a Syringe Shield. The disclosed shield is movable from a retracted position in which the needle is exposed, to an extended position in which the needle is covered. By movement into the extended position after use, the user is protected from inadvertent puncturing of the skin. Many other devices have similar properties, such as those disclosed in U.S. Pat. Nos. 4,702,738; 4,723,943; 4,737,144; 4,738,663; 4,747,837; 4,850,994; 4,801,295 and 4,908,023. Each of these devices discloses a different type of shield for covering a contaminated hypodermic needle after use.

U.S. Pat. Nos. 4,752,290 and 4,826,491 disclose Needle Bearing Medical Devices with Three-Position Shields. The disclosed devices are designed to move from a first position in which the needle of the syringe is covered, prior to use, to a second position in which the needle is exposed for use, and then to a third position in which the needle is again covered, after usage, so that the possibility of pricking is avoided.

Such devices, however, do not have universal applicability. There are many instances where a needle may be used other than with a hypodermic syringe.

A needle may be used to introduce a fluid into a "Y-site", i.e. a bifurcated tube having two input ports for receiving fluids to be dispensed into a patient, and one exit port connected to the patient. One input port of the Y-site is conventionally connected to a standard drip bottle, while the other is exposed. The exposed entry port has a diaphragm covering its opening. If a secondary fluid is to be dispensed through the Y-site, a second drip bottle having a tube which terminates in a needle is employed. The needle of that second drip bottle is inserted through the diaphragm of the Y-site, so that the secondary fluid may drip from the second drip bottle through the tube, past the diaphragm and into the patient. In these instances, it is sometimes necessary to retain the needle in position for an extended period, since the purpose of using a drip bottle is to provide fluids slowly over time.

Prior art devices, such as referenced above, lack suitable means for securing the syringe to a Y-site while in use, or for engagement of the Y-site to permit use while protecting the user. Furthermore, prior art devices do not permit the covering of the needle while it is inserted into a Y-site. The construction of these prior art protective devices, in fact, would prevent piercing the diaphragm while the protective sleeve is in its extended position.

One recent patent, U.S. Pat. No. 4,834,716, discloses a Protected Cannula (i.e. a needle) for use in dispensing fluids into a Y-site. The needle is carried within a fixed sleeve, which is used as a covering when the needle is inserted into the Y-site. While this serves to protect the fingers of the user from inadvertent puncture, it does not provide means for affirmatively securing the needle in place in the Y-site. Additionally, the sleeve is not movable with respect to the needle, thereby rendering the needle incapable of use in dispensing medicine directly into a patient's body.

Thus, there is a need for a needle protecting apparatus which may be used either with a Y-site or for dispensing fluids directly into a patient, while protecting against accidental puncturing of the user.

There is a further drawback to the prior art devices. When a hypodermic needle is used to dispense fluids intramuscularly, it is necessary to ensure that the needle extends only a given depth into the patient. Many times this is accomplished by limiting the length of the needle used to dispense the desired fluid. However, this requires the selection of differing needles for different applications, which, in turn requires practitioners to maintain supplies of needles of varying lengths. Since it is also often necessary to maintain supplies of needles having differing diameters, the need to maintain needles of different lengths may lead to the need to maintain several different diameters of needles each of differing lengths. This multiplication of needle sizes and diameters leads to increased cost.

Furthermore, if a shortage of one type of needle occurs, for example a short needle, usage of a needle having too great a length may cause the needle to enter the patient to an excessive depth, hitting a bone or otherwise injuring the patient or limiting the efficacy of the medicine dispensed. A shortage of longer needles would also be injurious, as the dispensed medicine may not be dispensed at the required depth. In either event, it would be useful to provide means for utilizing a standardized length of needle, without the risk of using a needle having insufficient or excessive length.

U.S. Pat. No. 4,356,822 shows a Syringe Assembly which permits the covering of only a portion of the exposed tip of the needle. Although the disclosed assembly permits the locking of a protective sleeve to cover an exposed needle tip, the sleeve is capable of movement in either direction along the barrel of the syringe, so that it is possible that, once covered, the tip may be exposed by movement of the sleeve out of its fully extended position.

Thus, there is still a need for a device for protecting the user from inadvertent exposure of a contaminated needle, by undesired movement of the protective sheath from its extended position into its retracted position after exposure to contaminants.

OBJECTS AND SUMMARY OF THE INVENTION

Accordingly, it is an object of the invention to provide a needle protecting assembly which overcomes the drawbacks of the prior art.

It is a further object of the invention to provide a needle protecting assembly which may be used to protect against accidental puncture when used either at a Y-site or in direct injections into the patient.

It is a still further object of the invention to provide a needle protecting assembly which may secure a needle in place when coupled to a Y-site.

It is another object of the invention to provide a needle protecting assembly which may be used to vary the length of the needle exposed beyond the edge of a protective sleeve, thereby permitting the varying of the depth to which the needle may penetrate the patient.

Briefly stated, there is provided a needle protective assembly which includes a ratchet and pawl arrangement for permitting the unidirectional movement of a protective sleeve along a body of a dispenser, such as a hypodermic syringe. The sleeve is adapted to cover a standard Y-site diaphragm, and includes a lock to secure the sleeve to the Y-site while in use. The assembly may also include indicia on the exterior thereof to measure the amount of needle exposed beyond the end of the sleeve, if the sleeve is not in its fully extended position. The assembly may further include a luer lock, for attaching the assembly to pre-existing standardized fittings.

In accordance with these and other objects of the invention, there is provided a protective assembly comprising: a hollow body having an interior and an exterior; means for retaining a conduit in communication with the interior of the hollow body, the conduit having a first end in communication with the interior of the hollow body, and a second, free, end extending on the exterior of the hollow body; a sleeve mounted on the exterior of the hollow body, the sleeve having a distal end and a proximal end; the distal end of the sleeve including means for receiving a receptacle with which the free end of the conduit may communicate; and means for permitting unidirectional movement of the sleeve along the exterior of the hollow body, in a direction towards the distal end of the sleeve from the proximal end thereof, the sleeve moving from a first, open position, in which the free end of the conduit is exposed beyond the distal end of the sleeve, to a second, closed, position in which the free end of the conduit is covered by the distal end of the sleeve; whereby the user may be protected against inadvertent contact with the free end of the conduit by the distal end of the sleeve when the sleeve is in the closed position.

According to feature of the invention, there is further provided a protective assembly comprising: a hollow body having an interior and a generally circular exterior; means for retaining a needle in communication with the interior of the hollow body, the needle having a first end in communication with the interior of the hollow body, and a second, free, end extending on the exterior of the hollow body; a cylindrical sleeve mounted on the exterior of the hollow body, the sleeve having a distal end and a proximal end; the distal end of the sleeve including means for receiving a receptacle with which the free end of the needle may communicate; and means for permitting unidirectional movement of the sleeve along the exterior of the hollow body, in a direction towards the distal end of the sleeve from the proximal end thereof, the sleeve moving from a first, open position, in which the free end of the needle is exposed beyond the distal end of the sleeve, to a second, closed, position in which the free end of the needle is covered by the distal end of the sleeve; whereby the user may be protected against inadvertent contact with the free end of the needle by the distal end of the sleeve when the sleeve is in the closed position.

The above, and other objects, features and advantages of the present invention will become apparent form the following description read in conjunction with the accompanying drawings, in which like reference numerals designate the same elements.

DETAILED DESCRIPTION OF THE PREFERRED EMBODIMENT

Figure 1:
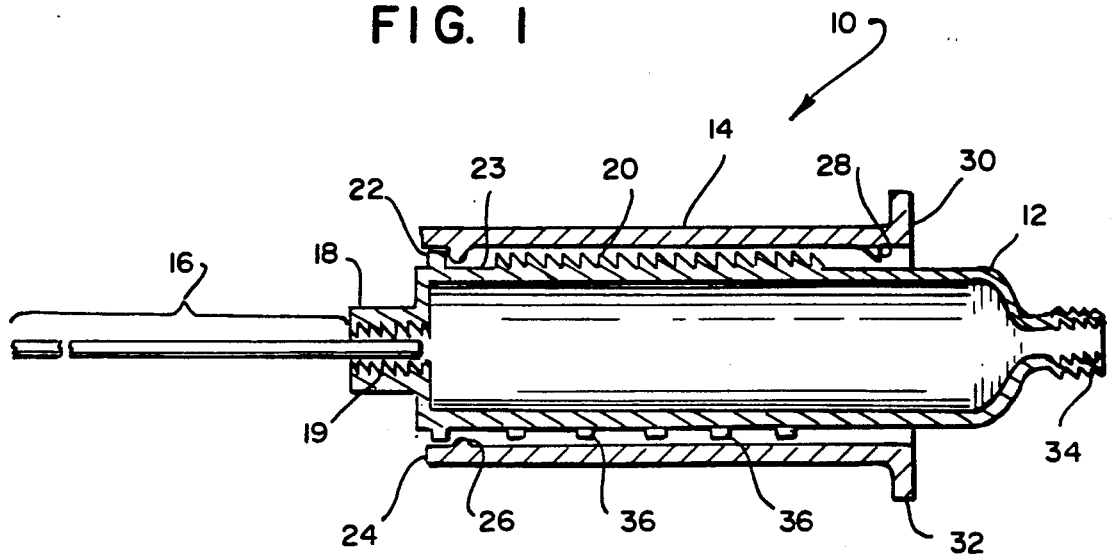
FIG. 1 is a cross-section of a protective assembly of the preferred embodiment of the invention, shown prior to use.

Referring now to FIG. 1, there is shown, generally at 10, a protective assembly, in accordance with the invention. Protective assembly 10 includes a hollow body 12 and a generally cylindrical sleeve 14 slidably mounted thereon. A conduit, such as a needle 16 is attached to a forward end 18 of hollow body 12, providing communication between the interior and exterior thereof. Preferably, needle 16 is mounted by means of a standard screw and thread arrangement 19, to permit the exchange of needles from one gauge or length to another. Such needle mounting also could be effected with a luer lock arrangement.

A series of angled ratchet teeth 20 are disposed on the exterior of hollow body 12, preferably in a linear array. Teeth 20 are arranged so that they slope away from forward end 18 of hollow body 12.

Hollow body 12 also includes a stop 22 fixed near forward end 18, and spaced from the end of teeth 20 by a gap 23.

Cylindrical sleeve 14 has a forward, or distal, end 24 proximate to which is mounted a resilient locking member, such as ribs 26. A resilient angled pawl 28 is mounted at the opposite, or proximal, end 30. Proximal end 30 preferably includes a wide flange 32.

Figure 2:
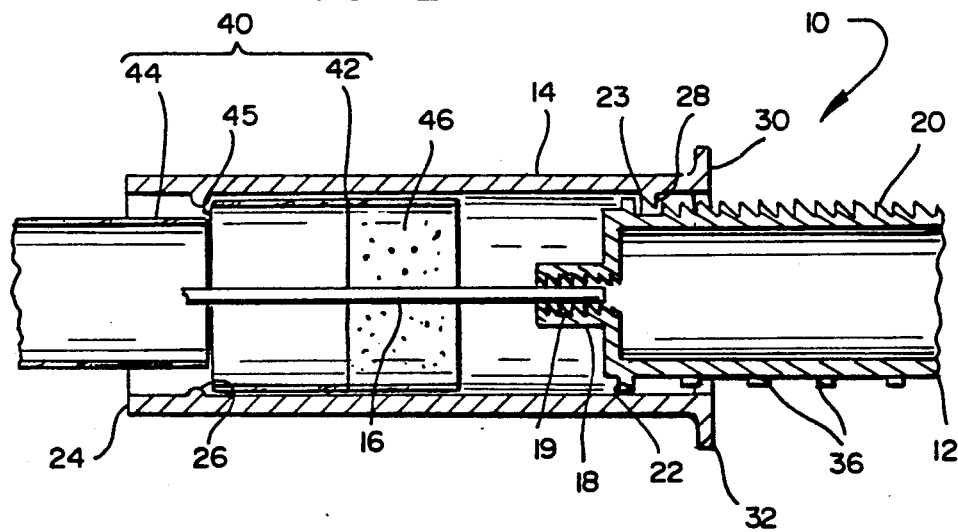
FIG. 2 is a cross-section of a protective assembly of the embodiment of FIG. 1, shown when coupled to a standard Y-site entry port.

In use, protective assembly 10 may be used in a multipurpose device, useful as either a hypodermic syringe or as means for dispensing fluids into a Y-site drip tube (see FIG. 2).

If protective assembly 10 is to be used as a hypodermic device, it may be attached to a standard hypodermic syringe with a male luer lock 34, disposed on the rearward end of hollow body 12. Fluid contained within that hypodermic syringe (not shown) could be dispensed from protective assembly 10 through needle 16. During this procedure, sleeve 14 is maintained in a retracted position, such as shown in FIG. 1. In the retracted position, needle 16 is fully exposed, and sleeve 14 is completely disposed behind forward end 18 of hollow body 12. This enables the user to change needles, if desired, in known fashion.

When sleeve 14 is in its retracted position, pawl 28 is out of engagement with ratchet teeth 20, and ribs 26 are disposed behind stop 22, inhibiting forward movement of sleeve 14.

Once a fluid is drawn into hollow body 12, it may be dispensed in normal fashion through needle 16 by means of pressure exerted on the hypodermic syringe. Once protective assembly 10 has been used, and it is no longer necessary to use needle 16, sleeve 14 may be slid forward, i.e. towards distal end 24 by exerting axial pressure on flange 32. This pressure causes sleeve 14 to move towards forward end 18 of hollow body 12, and deforms ribs 26 so that they move over stop 22, and permit the further, forward, movement of sleeve 14. The complementary slopes of teeth 20 and pawl 28 ensure that sleeve 14 may only move in a single direction, and that the unidirectional movement is towards the distal end of sleeve 14.

If protective assembly 10 is used to dispense fluids into a patient intravenously, then sleeve 14 will be deployed only on completion of use. At that time, sleeve 14 will be moved axially forward until pawl 28 thereof engages stop 22. Stop 22 is configured so that it prevents further forward movement of sleeve 14 when pawl 28 engages stop 22. In this position, sleeve 14 will cover needle 16, thereby protecting the user from inadvertently pricking his fingers after usage of the needle. This avoids any potential transfer of contagion from the patient to the user. Additionally, the ratchet and pawl arrangement 20 and 28 permits movement of sleeve 14 only in the forward direction, preventing inadvertent exposure of needle 16 once sleeve 14 has been fully extended.

Limiting the movement of sleeve 14 in the forward direction provides an additional benefit. When the user is dispensing fluids into the patient, he may place a rearward force on flange 32 to ensure that sleeve 14 does not move forward at an undesired time. Since sleeve 14 cannot move rearward, that small pressure does not actually move sleeve 14, but merely maintains it in its fully (or partly) retracted position until it is desired to deploy it to its extended position.

The same procedure may be followed if protective assembly 10 is to be used to dispense fluids intramuscularly, but there is an added benefit. One of the problems in dispensing fluids intramuscularly is that the needle used to do so may penetrate to an undesired depth, either too shallow or too deep. Currently, a practitioner may limit the depth of the penetration of the needle by selecting a needle whose length is exactly right for the particular application. However, that requires the practitioner to maintain supplies of needles of varying length, which increases costs in inventory, and storage.

With the use of protective assembly 10, the practitioner may use needles of a fixed length and yet achieve the desired depth limitations. The user first ascertains the desired depth for the application, and then moves sleeve 14 forward until a desired length of needle 16 is left uncovered thereby. Since sleeve 14 may only move unidirectionally in the forward direction, distal end 24 of sleeve 14 will act as a stop in the penetration of the patient, thereby limiting the depth of penetration of needle 16.

The measurement of the desired length of needle 16 may be facilitated by indicia 36 disposed on the exterior of hollow body 12. While indicia 36 are shown as raised, they may be in any form, such as painted on or formed within teeth 20 as raised letters or by coloring within the walls of hollow body 12. Furthermore, to facilitate the axial movement of sleeve 14, and prevent the twisting thereof, sleeve 14 and body 12 may be formed with a tongue and groove arrangement, wherein a tongue (not shown) disposed on either member may slide in a groove on the other member, thereby preventing the relative turning of the two members.

Figure 3:
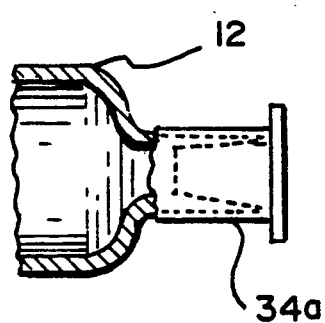
FIG. 3 is a fragmentary right end portion view partly in section, of the hollow body depicting a luer lock fitting thereon.

Thus far, protective assembly 10 has been described solely in its capacity to work with a hypodermic syringe to dispense fluids directly into the body of a patient. It may also be used to dispense fluids into a drip tube, such as a Y-site. In this capacity, protective assembly 10 would be attached to a source of fluid to be dispensed by means of luer lock fitting 34a as shown in FIG. 3.

The use of protective assembly 10 with a Y-site is shown in FIG. 2. As shown, a Y-site 40 includes a large head portion 42, and a reduced diameter portion 44. Head portion 42 and reduced diameter portion 44 are separated by a shoulder 44. Reduced diameter portion 44 leads to a tube (not shown) which may be inserted into the body of a patient. The end of head portion opposite shoulder 44 contains a penetrable member, such as a diaphragm 46. Diaphragm 46 is adapted to be air-tight, but capable of penetration by a sharp point, such as needle 16. The configuration and structure of Y-site 40 is well known, and bears no further explanation or discussion here.

Protective assembly may be used to engage Y-site 40. If protective assembly 40 is used in this fashion, luer lock 34 (not shown in FIG. 2) of hollow body 12 engages a mating lock on a fluid source (also not shown). Sleeve 14 is moved into its completely extended position, in which pawl 28 engages stop 22, and the tip of needle 16 is completely covered by distal end 24 of sleeve 14. In this position, sleeve 14 is no longer capable of movement in either axial direction.

Needle 16 may be inserted through diaphragm 46, to permit communication between the interior of hollow body 12 and Y-site 40, thereby permitting the dispensing of fluids therethrough. Since sleeve 14 is extended beyond the tip of needle 16, the interior circumference of sleeve 14 may be used as a guide, so that needle 16 penetrates the center of diaphragm 46. Additionally, ribs 26 engage shoulder 44, thereby inhibiting the inadvertent removal of protective assembly 10 from Y-site 40. This serves to lock the two together, while permitting the later desired removal of protective assembly 10 from Y-site 40 when its utility is over.

Thus, protective assembly 10 may be used to protect a user from inadvertent puncturing by the tip of needle 16, while also safeguarding against the disengagement of protective assembly 10 from a Y-site.

It will be appreciated that the illustrated embodiment is not drawn to scale, but for ease of illustration. In the preferred embodiment, body 12 is 1.875 inches (appx. 4.75 cm) long, with an interior diameter of 0.170 inches (appx. 4.3 mm). Stop 22 is a raised circular abutment having an axial length of 0.90 inches (appx. 2.29 cm). Ratchet teeth 20 are sloped at a 20° angle, with a forward height of 0.013 inches (appx. 3.3 mm) and a length of 0.036 inches (appx. 0.9 mm). Gap 23 is 0.065 inches long (appx. 1.7 mm)

Sleeve 14 is preferably 1.6875 inches long (appx. 4.3 cm), with an external circumference of 0.465 inches (appx. 1.2 cm) and an interior circumference of 0.34 inches (appx. 8.6 mm). Pawl 28 is raised approximately 0.03 inches (appx. 0.8 mm) from the interior wall of sleeve 14, and is approximately 0.06 inches (appx. 1.5 mm) long. Ribs 26 are preferably manufactured as a single arcuate rib on the interior circumference of sleeve 14, having a raised height of 0.015 inches (appx. 0.4 mm), and a radius of 0.031 inches (appx. 0.8 mm), with a length of 0.055 inches (appx. 1.4 mm).

In the preferred embodiment, protective assembly 10 is manufactured of a soft plastic, such as polyethylene, although polypropylene is believed to be acceptable as well.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

For example, rather than using raised flange 32 on the proximate end 30 of sleeve 14 for pushing sleeve 14 forward, it is possible to use a knurled finger grip on the exterior surface of sleeve 14.

It will also be appreciated that, while in the preferred embodiment ratchet teeth 20 are disposed on hollow body 12, and pawl 28 is disposed on the interior of sleeve 14, these two members may be reversed, with a pawl positioned on body 12, and teeth on the interior of sleeve 14.

What is claimed is:

1. A protective medical device comprising
    an elongated hollow body, there being a needle element carried at one end of the body and extending longitudinally a distance beyond said one end,
    a sleeve mounted encirclingly on the body and having a sleeve retracted position wherein a first end of said sleeve is proximate the body one end, and a sleeve second end is proximate a body second end,
    said sleeve being slidable on said body from its retracted position in a sleeve extending travel advancing its second end toward the body one end to position the first sleeve end beyond a tip end of the needle element for the purpose optionally of protecting against inadvertent user contact with the said tip end, or removably mounting the sleeve to a Y-site structure at a securement location distant from that at which the needle element would have passage through a diaphragm covering an entry to the Y-site structure during sleeve mounting to the Y-site, said sleeve having resilient locking means thereon proximal the said first end thereof for removably locking the medical device to the Y-site structure,
    means for preventing retraction travel of said sleeve from any extended travel position thereof, said means including a linear arrayed series of teeth carried on one of an exterior surface of said body and an inner surface of said sleeve, and a pawl carried on the other of said exterior and interior surfaces, said pawl being urged into locking engagement with the teeth of said series by a force imposed on the sleeve tending to retract it, and
    a fitting at the second end of the hollow body for connecting it with another medical device.

2. The protective medical device of claim 1 in which the hollow body second end fitting is a luer lock.

3. The protective medical device of claim 1 in which the hollow body is fitted with a luer lock at the said one body end thereof, said luer lock being receptive of the needle element.

* * * * *